(12) United States Patent
Sun et al.

(10) Patent No.: US 6,833,698 B2
(45) Date of Patent: Dec. 21, 2004

(54) METHODS OF DECOUPLING DIFFUSION EFFECTS FROM RELAXATION TIMES TO DETERMINE PROPERTIES OF POROUS MEDIA CONTAINING FLUIDS

(75) Inventors: Boqin Sun, Concord, CA (US); Keh-Jim Dunn, San Ramon, CA (US)

(73) Assignee: ChevronTexaco U.S.A. Inc., San Ramon, CA (US)

(*) Notice: Subject to any disclaimer, the term of this patent is extended or adjusted under 35 U.S.C. 154(b) by 0 days.

(21) Appl. No.: 10/150,284

(22) Filed: May 15, 2002

(65) Prior Publication Data

US 2003/0214287 A1 Nov. 20, 2003

(51) Int. Cl.[7] ............................................. G01V 3/00
(52) U.S. Cl. ............................................ 324/303
(58) Field of Search ............................ 324/300, 303, 324/307, 309, 318

(56) References Cited

U.S. PATENT DOCUMENTS 5,023,551 A    6/1991  Kleinberg et al. .......... 324/303
5,291,137 A  * 3/1994  Freedman ................... 324/303

(List continued on next page.)

FOREIGN PATENT DOCUMENTS

WO        01/42817 A1   6/2001   ............ G01V/3/32

OTHER PUBLICATIONS

Keh–Jim Dunn, Gerald A. LaTorraca, "The Inversion of NMR Log Data Sets with Different Measurement Errors," *Journal of Magnetic Resonance*, pp. 140,153–161 (1999).

(List continued on next page.)

Primary Examiner—Christopher W. Fulton
Assistant Examiner—Dixomara Vargas

(57) ABSTRACT

Novel pulse sequences are used to probe the properties of porous media, such as are found in subterranean formations and core samples. This use allows diffusion effects to be uncoupled from the overall $T_2$ relaxation time of the sample. Properties such as internal field gradient and distribution of diffusion coefficients may be determined. A series of pulse sequences are applied to the media to be evaluated. The series of pulse sequences include first and second windows. The first windows include pulse sequences have varying characteristics, such as increasing echo spacing, while the second windows preferably utilize similar pulse sequences which have very small echo spacing. Apparent internal field gradient distribution and apparent diffusion coefficient may be determined as a function of $T_2$ relaxation time. These properties are readily visualized in a two-dimensional map with a first axis being the apparent internal field gradient or alternatively the diffusion coefficient of pore fluids, a second axis being the $T_2$ relaxation times, and the vertical amplitudes being proportional to the proton population. Other properties which may be determined from use of this method include porosity, pore size distribution, oil and water saturation, oil viscosity, oil wettability, and permeability. Also, a method for determining and plotting a $T_1$-MAS 2D spectrum is provided where $T_1$ relaxation time and chemical shift are plotted on x,y axes while intensity of proton population is displayed along a third axis.

27 Claims, 10 Drawing Sheets

U.S. PATENT DOCUMENTS

| | | | | |
|---|---|---|---|---|
| 5,363,041 | A | | 11/1994 | Sezginer ..................... 324/303 |
| 5,381,092 | A | * | 1/1995 | Freedman ................... 324/303 |
| 5,486,762 | A | * | 1/1996 | Freedman et al. .......... 324/303 |
| 5,517,115 | A | | 5/1996 | Prammer .................... 324/303 |
| 5,557,200 | A | * | 9/1996 | Coates ....................... 324/303 |
| 5,585,720 | A | | 12/1996 | Edwards ..................... 324/309 |
| 5,796,252 | A | | 8/1998 | Kleinberg et al. .......... 324/303 |
| 6,005,389 | A | | 12/1999 | Prammer .................... 324/303 |
| 6,049,205 | A | * | 4/2000 | Taicher et al. .............. 324/303 |
| 6,069,477 | A | | 5/2000 | Chen et al. ................. 324/303 |
| 6,105,690 | A | * | 8/2000 | Biglin et al. .................. 175/48 |
| 6,133,735 | A | * | 10/2000 | Hurlimann et al. ......... 324/303 |
| 6,144,874 | A | * | 11/2000 | Du ............................. 600/413 |
| 6,147,489 | A | * | 11/2000 | Freedman et al. .......... 324/303 |
| 6,166,543 | A | * | 12/2000 | Sezginer et al. ............ 324/303 |
| 6,255,818 | B1 | | 7/2001 | Heaton et al. .............. 324/303 |
| 6,316,940 | B1 | | 11/2001 | Akkurt ....................... 324/303 |
| 6,331,775 | B1 | * | 12/2001 | Thern et al. ................ 324/303 |
| 6,344,744 | B2 | * | 2/2002 | Taicher et al. .............. 324/303 |
| 6,366,087 | B1 | | 4/2002 | Coates et al. ............... 324/303 |
| 6,369,567 | B1 | | 4/2002 | Song et al. ................. 324/303 |
| 6,522,136 | B1 | * | 2/2003 | Hurlimann et al. ......... 324/303 |
| 6,559,639 | B2 | * | 5/2003 | Minh et al. ................. 324/303 |
| 6,570,382 | B1 | * | 5/2003 | Hurlimann et al. ......... 324/303 |
| 6,573,715 | B2 | * | 6/2003 | King et al. ................. 324/303 |
| 6,577,125 | B2 | * | 6/2003 | Prammer et al. ........... 324/303 |

OTHER PUBLICATIONS

Keh–Jum Dunn, "Enhanced Transverse Relaxation in Porous Media due to Internal Field Gradients," *Journal of Magnetic Resonance,* pp. 156, 1–10 (2002).

K–J Dunn, M. Appel, J.J. Freeman, J.S. Gardner, G.J. Hirasaki, J.L. Shafer, and G. Zhang "Interpretation of Restricted Diffusion and Internal Field Gradients in Rock Data," Published in the Proceedings of $42^{nd}$ Annual Symposium of Society of Professional Well Log Analysts, Houston, TX (2001), Paper AAA.

M. D Hurlimann, L. Venkataramanan, C. Flaum, P. Speier, C. Karmonik, R. Freedman, and N. Heaton, "Duffusion–Editing: New NMR Measurement of Saturation and Pore Geometry," $43^{rd}$ Annual SPWLA Meeting in Oiso, Japan, Jun. $2^{nd}$ to Jun. $5^{th}$, 2002, pp. 1–14.

\* cited by examiner

Figure 8A
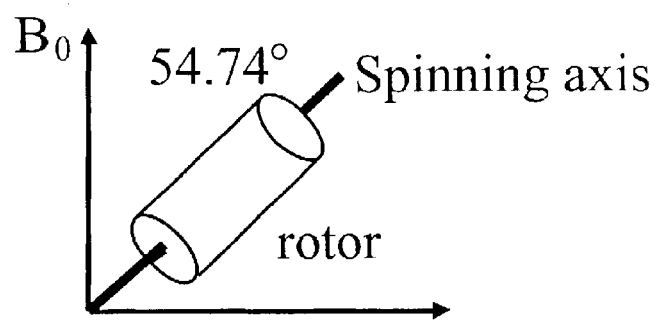
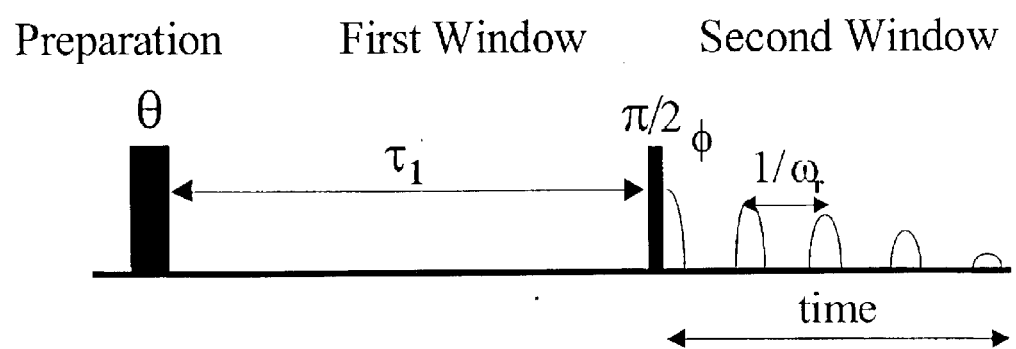
Figure 8B

METHODS OF DECOUPLING DIFFUSION EFFECTS FROM RELAXATION TIMES TO DETERMINE PROPERTIES OF POROUS MEDIA CONTAINING FLUIDS

FIELD OF THE INVENTION

This invention relates to methods of applying external magnetic fields and Radio Frequency (RF) pulses to fluid saturated porous media and subsequently receiving and analyzing signals therefrom to determine properties of the fluid saturated porous media, and more particularly, to methods which utilize Nuclear Magnetic Resonance (NMR) to analyze properties of subterranean formations and borehole core samples.

BACKGROUND OF THE INVENTION

NMR instruments are known to be used which employ pulsed RF fields to excite porous media containing fluids in pore spaces thereby inducing signals to be emitted from the fluid and porous media. The emitted signals are then analyzed to determine important properties of the fluid and porous media. Emitted signals of particular value include proton nuclear magnetic resonance signals. These signals are analyzed to provide data including porosity, pore size distribution of the porous media, percentage oil and water content, permeability, fluid viscosity, wettability, etc.

NMR measurements can be done using, for example, the centralized MRIL.RTM. tool made by NUMAR, a Halliburton company, and the sidewall CMR tool made by Schlumberger. The MRIL.RTM. tool is described, for example, in U.S. Pat. No. 4,710,713 to Taicher et al. Details of the structure and the use of the MRIL.RTM. tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115, 5,557,200 and 5,696,448. A Schlumberger CMR tool is described, for example, in U.S. Pat. Nos. 5,055,787 and 5,055,788 to Kleinberg et al.

The content of the above patents is hereby expressly incorporated by reference.

Proton nuclear magnetic resonance signals measured from a fluid-saturated rock contains information relating to the bulk and surface relaxation and diffusion coefficients of pore fluids, the pore size distribution, and the internal magnetic field gradient distribution within pore spaces. These multiple pieces of information are often coupled together in a complicated fashion making it very difficult to sort out the value of each of the aforementioned individual physical quantities.

Diffusion may be qualitatively described as the process by which molecules move relative to each other because of their random thermal motion. This diffusive action of molecules enhances the relaxation rate of NMR signals in a magnetic field gradient.

For fluids in rock pores, three independent mechanisms are primarily responsible for the relaxation or decay of magnetic resonance signals (Coates, G. R., Xiao, L. and Prammer, M. G., NMR Logging Principles and Applications, p. 46, (1999)):

bulk fluid relaxation processes, which determine the value for $T_1$ and $T_2$ for bulk fluids;
surface relaxation which affects both $T_1$ and $T_2$; and
diffusion in the presence of magnetic field gradients, which only affects $T_2$ relaxation.

All three processes act in parallel, and the apparent $T_1$ and $T_2$ of pore fluids are given by:

$$\frac{1}{T_{1,app}} = \frac{1}{T_{1B}} + \frac{1}{T_{1S}}; \tag{1}$$

$$\frac{1}{T_{2,app}} = \frac{1}{T_{2B}} + \frac{1}{T_{2S}} + \frac{1}{T_{2D}}; \tag{2}$$

$$\frac{1}{T_{1,2S}} = \rho_{1,2} \frac{S}{V}; \tag{3}$$

$$\frac{1}{T_{2D}} = \frac{1}{3}\gamma^2 g^2 D\tau^2; \tag{4}$$

where:

$T_{1,app}$ is the measured apparent longitudinal relaxation time of the pore fluid;
$T_{1B}$ is the longitudinal relaxation time of the pore fluid in bulk phase, i.e., when it is an infinite fluid medium not restricted by pore walls;
$T_{1S}$ is the longitudinal relaxation time of the pore fluid due to the surface relaxation mechanism;
$T_{2,app}$ is the measured apparent transverse relaxation time of the pore fluid;
$T_{2B}$ is the transverse relaxation time of the pore fluid in bulk phase, i.e., when it is an infinite fluid medium not restricted by pore walls;
$T_{2S}$ is the transverse relaxation time of the pore fluid due to the surface relaxation mechanism; and
$T_{2D}$ is the equivalent relaxation time of the pore fluid of the enhanced relaxation rate due to diffusion of spins in a magnetic field gradient;

where $\gamma$ is the gyromagnetic ratio, $\tau$ is the time between the initial $\pi/2$ pulse and the subsequent $\pi$ pulse, or half the echo spacing in a Carr-Purcell-Meiboom-Gill (CPMG) (Carr, H. Y. and Purcell, E. M., Phys. Rev. 94, 630 (1954) and Meiboom, S. and Gill, D., Rev. Sci. Instrum. 29, 668 (1958)) experiment, $\rho_{1,2}$ is the surface relaxivity for $T_{1,2}$ surface relaxation; S is the area of the pore surface; V is the volume of the pore; g is the magnetic field gradient, and D is the diffusion coefficient of the spins in the fluid.

Thus the measured magnetization decay, i.e., the spin echo amplitude as a function of time $t_i$ (the decay time for the i-th echo) for a single pore size system saturated with a single pore fluid can be expressed as:

$$\begin{aligned}\frac{M(t_i)}{M_0} &= \exp\left[-\frac{t_i}{T_{2B}} - \frac{t_i}{T_{2S}} - \frac{t_i}{T_{2D}}\right] \\ &= \exp\left[-\frac{t_i}{T_{2B}} - \frac{t_i}{T_{2S}} - \frac{1}{3}\gamma^2 g^2 \tau^2 D t_i\right].\end{aligned} \tag{5}$$

Note that Eq.(3) is valid for the fast diffusion limit, i.e., when the diffusion time for a spin to traverse the pore is much shorter than the surface relaxation time. Eq.(4) is strictly valid only for an infinite medium and approximately valid in fluid-saturated porous media when the Gaussian approximation for the phase distribution of spins is satisfied (Dunn, K. J. et al, SPWLA 42$^{nd}$ Annual Symposium, Paper AAA, Houston, Tex., June 17–20 (2001); and Dunn, K. J., Magn. Reson. Imaging, 19, 439, (2000)). In the present discussion, it is assumed that such Gaussian approximation is valid. Deviation of the physical quantities from their expected values may be attributed, in part, to the failure of such assumption.

Natural fluid-saturated rocks generally have multiple pore sizes. If the surface relaxation strength is reasonably strong (i.e., $\rho \sim 10\ \mu m/s$), the spins in the pore fluid can only diffuse a short distance of a few pores, the spins at each pore relax more or less independently of the spins in other pores in a diffusion decoupled situation.

Thus, the spin echo amplitude as a function of time $t_i$ for a multiple pore size system when there is no magnetic field gradient can be expressed as:

$$\frac{M(t_i)}{M_0} = \sum_j f_j e^{-t_i/T_{2j}} \tag{6}$$

where the first term in the exponent of Eq.(5) is neglected because $T_{2B} \gg T_{2S}$, and $t_i$ is the decay time for the i-th echo in a CPMG experiment, $f_j$ is the volume fraction of the pores characterized by a common $T_2$ relaxation time $T_{2j}$, and $1/T_{2j} = \rho_2 S_j/V_j$ (where $S_j$ is the pore surface area and $V_j$ is the pore volume of pore size j). $T_{2j} = \alpha_j/\rho_2$ with $\alpha_j = V_j/S_j$ as a measure of the pore size.

The LHS of Eq.(6) can be obtained from a CPMG measurement, whereas the volume fractions $f_j$ on the RHS of Eq.(6) are to be solved from the data analysis. This problem is usually treated by assuming a set of pre-selected $T_{2j}$ values equally spaced on a logarithmic scale and solving for the amplitude $f_j$ associated with $T_{2j}$. The solution obtained is called the $T_2$ distribution (i.e., $f_j$ vs $T_{2j}$). This mathematical procedure of obtaining the $T_2$ distribution is common in NMR relaxation data analysis and is referred to as an inversion process. Since $T_{2j} = \alpha_j/\rho_2$ in the fast diffusion limit, the $T_2$ distribution frequently reflects the pore size distribution of the rock.

For a fluid-saturated porous medium in a magnetic field gradient, the problem becomes a bit more complicated. The magnetic field inhomogeneities can come from an externally applied field gradient, which is uniform over the pore scale, and/or from local field gradients which have a spatial variation across individual pores. The latter is caused by the magnetic susceptibility contrast between the solid matrix and pore fluids.

If the externally applied magnetic field gradient is much larger than the local field gradients in the pore space due to magnetic susceptibility contrast, the spin echo amplitude can be expressed as a function of time $t_i$ for a multiple pore size system as:

$$\frac{M(t_i)}{M_0} = \sum_j f_j e^{-t_i/T_{2j}} e^{-\gamma^2 g^2 \tau^2 D t_i/3}. \tag{7}$$

Note that the enhanced relaxation term due to diffusion, $e^{-\gamma^2 g^2 \tau^2 D t_i/3}$, has a fixed field gradient g determined by the externally applied field gradient. It is not related to the pore sizes, and can be pulled out of the summation sign. Thus, this term can be decoupled from the summation over different pore sizes, which makes the analysis relatively easy.

Frequently, the probed zone of an NMR logging tool has a magnetic field gradient distribution, S(g), where the gradient varies over a scale much larger than the pore scale such that the value g can be treated as a constant over the dimension of a representative volume element of the probed zone. In this case, it is the same as Eq. (7), i.e., for each volume element, it has a constant g value. Thus, the enhanced relaxation term due to diffusion can be pulled out of the summation over different pore sizes and can be expressed in the following form:

$$\frac{M(t_i)}{M_0} \int S(g) e^{-\gamma^2 g^2 \tau^2 D t_i/3} dg \sum_j f_j e^{-t_i/T_{2j}} \tag{8a}$$

This is not the case, however, when the local field gradients become significant or dominant. These internal field gradients are affected by the pore shapes and sizes, and vary over the pore scale. They cannot be decoupled from the summation over different pore sizes. The spin echo amplitude as a function of time $t_i$ is now expressed as:

$$\frac{M(t_i)}{M_0} = \sum_j f_j e^{-t_i/T_{2j}} \int_j P_j(g) e^{-\gamma^2 g^2 \tau^2 D t_i/3} dg \tag{8b}$$

where $P_j(g)$ is the volume fraction which has a gradient value of g within the pore of size j, and $$\int_j P_j(g) dg = 1 \tag{9}$$

is normalized to 1.

The fact that this enhanced relaxation term due to diffusion cannot be decoupled from the summation presents a problem to the data analysis, namely, information cannot be obtained on the internal field gradient distribution as a function of pore size, and thus corrections cannot be made on its adverse effect on data analysis.

Similar problems arise when information is to be obtained regarding brine and crude oil saturated rocks from regular CPMG measurements, where the internal field gradients are small and are not a concern, but the crude oil also has a $T_2$ distribution which is to be solved. The spin echo amplitude as a function of time $t_i$ is now expressed as:

$$\frac{M(t_i)}{M_0} = \sum_j \left( f_{w,j} e^{-t_i/T_{2j}} e^{-\gamma^2 g^2 \tau^2 D_w t_i/3} + \right. \tag{10}$$
$$\left. f_{o,j} e^{-t_i/T_{2j}} \int P(D_{oil}) e^{-\gamma^2 g^2 \tau^2 D_{oil} t_i/3} dD_{oil} \right)$$

where $f_{w,j}$ is the volume fraction for brine and $f_{o,j}$ is the volume fraction for crude oil, and the diffusion coefficient of the crude oil, $D_{oil}$, has a distribution, $P(D_{oil})$, and $$\int P(D_{oil}) dD_{oil} = 1 \tag{11}$$

is normalized to one.

Again, in Eq.(10), the enhanced relaxation term due to diffusion for oil cannot be pulled out of the summation because it is related to the summation indices in the following manner:

$$D_{oil,j} = a \frac{T_K}{\eta_j} \tag{12}$$

$$T_{2,j} = b \frac{T_K}{\eta_j} \tag{13}$$

and thus $$D_{oil,j} = \frac{a}{b} T_{2,j} \tag{14}$$

following the Constituent Viscosity Model (CVM) suggested by Freedman et al. (Freedman, R., Sezginer, A., Flaum, M., Matteson, A., Lo, So., and Hirasaki, G. J., SPE Paper 63214, Society of Petroleum Engineers, Dallas, Tex. (2000)), where a and b are proportional constants, $T_K$ is the absolute temperature in Kelvin, and $\eta_j$ is the constituent viscosity related to the chosen $T_{2j}$ and $D_{oil,j}$.

Although the enhanced relaxation term due to diffusion for water is not related to the summation indices because the diffusion coefficient for water is a single value and does not have a distribution, it cannot be treated separately. In fact, even though the diffusion coefficient for water is a single value, it can also have an apparent distribution of diffusion coefficients due to the following reasons:

(1) effect of noise which prevents the result from having a sharp and well-defined value,
(2) restricted diffusion effect from different pore sizes, and
(3) unknown internal field gradients which superimpose upon any fixed gradient over the pore dimension and lump their effect on the diffusion coefficient when a fixed gradient value is used in the analysis.

Accordingly, there is a need for one or more methods which uncouple the entangled information due to diffusion effects received during NMR analysis so that determinations can be made regarding properties of porous media and fluids contained within pore spaces from a subterranean formation or from a core sample of rock. Furthermore, there is a need to display these results in a manner that is particularly effective in visualizing the results of the analysis.

SUMMARY OF THE INVENTION

The present invention includes a method for analyzing the properties of a porous medium containing fluids. The method includes the following steps. A static magnetic field $B_0$ is applied to a porous medium containing fluid in pore spaces to polarize spins of protons in the porous medium and fluids and create an overall magnetization. A series of differentiated sequences of radio frequency (RF) pulses and possible gradient pulses is applied to the porous medium and fluids contained therein at the resonance frequency of the protons and at a given external magnetic field to excite the magnetization. The pulse sequences have a preparation part followed by a first window of a time length $t_0$ and a second window, wherein the portion of the pulse sequence in the first window of at least one pulse sequence is differentiated by at least one differentiating variable $v_d$ from the portion of the pulse sequence in the first window of another of the pulse sequences.

Induced resonance signals are acquired from the porous medium and fluids contained therein during the second windows of the pulse sequences. The resonance signals are acquired as a function of $t_i$, $PA_1(t_i)$, and $v_d$, where $t_i$ is the time of the $i_{th}$ spin echo in the second window as measured from initiation of that second window, $PA_1(t_i)$ is the spin echo amplitude, and $v_d$ is the value of the differentiating variable. The acquired induced resonance signals, acquired as a function $t_i$, $PA_1(t_i)$, and $v_d$, are processed to determine properties of the porous medium and fluids contained therein as a function of $T_2$, one of g and D, and $PA_3$, where $T_2$ is the transverse relaxation time of the protons, g is the internal field gradient in the pore spaces, D is the diffusion coefficient of the fluids in the pores, and $PA_3$ is an amplitude distribution proportional to proton population. The use of the differentiated pulse sequences in the first windows of the pulse sequences creates differentiated decay amplitudes at the initiation of the second windows. The acquisition of echo signals in the second windows beginning at a time $t_0$ and accommodates the uncoupled determination of the quantities of transverse relaxation time $T_2$ of protons, either the internal field gradients g or the diffusion coefficient D, and the amplitude proportional to proton population $PA_3$.

Ideally, the values $T_2$, one of g and D, and $PA_3$ are plotted on orthogonal axes to produce a 2D NMR plot to provide visualization of properties of the porous medium and fluids contained therein.

Another method for analyzing the properties of a porous medium containing fluids is also disclosed. A static magnetic field $B_0$ is applied to a porous medium containing fluids in pore spaces to polarize spins of protons in the porous medium and fluids and create an overall magnetization. Then, a technique called magic angle spinning is applied to the porous medium followed by a series of rotor synchronized radio frequency (RF) pulses. The RF pulses include a $\theta$ pulse followed by a $\pi/2$ pulse at time $\tau_1$. Free Induction Decay (FID) signals are acquired from the porous medium and fluids contained therein as a function of recovery time $\tau_1$.

The acquired FID signals are Fourier transformed to obtain a plurality of proton chemical shift spectra at different recovery times $\tau_1$ and further inverted to obtain an amplitude which is proportional to proton population as a function of proton chemical shift and $T_1$ relaxation time.

Subsequently, the values $T_1$ relaxation time, proton chemical shift and the amplitude proportional to the proton population are plotted on orthogonal axes to produce a 2D NMR plot for visualization of properties characteristic of the porous medium and fluids contained therein.

The present invention further includes storing the above analytical methods on a computer readable media for implementation by NMR instrumentation. Further, the above methods may be practiced on core samples in a laboratory. The determination of internal field gradient and/or diffusion coefficient distribution may be made as part of a downhole logging operation in a wellbore.

It is an object of the present invention to provide novel pulse sequences which allow diffusion effects, due to significant internal field gradients found in pore spaces of porous media, to be decoupled from overall $T_2$ relaxation times.

It is another object to provide a method for determining diffusion coefficient distribution as a function of $T_2$ relaxation time in a porous medium containing fluids.

It is yet another object to provide a novel series of pulse sequences wherein each pulse sequences includes a preparation part, a first window and a second window. The portion of the pulse sequences in the first windows of the series of pulse sequences are differentiated from one another so that the spin echo amplitudes are differentiated from each other at the initiation of each of the second windows thereby uncoupling the diffusion effect from the $T_2$ relaxation time.

It is a further object of the present invention to provide a mathematical method for handling the data contained in the attenuated $T_2$ amplitude due to the diffusion effect, and to process such information into a useful multi-dimensional representation for petrophysical analysis.

It is yet another object to provide a method which removes or minimizes the effects of the internal magnetic field distribution in porous media, such as rocks, in the analysis of the proton NMR relaxation data obtained from borehole logging measurements to thereby extract information about the properties of the pore fluids saturating the porous media from a proton NMR signal distorted by the presence of internal field gradients and molecular diffusion.

BRIEF DESCRIPTION OF THE DRAWINGS

These and other objects, features and advantages of the present invention will become better understood with regard to the following description, pending claims and accompanying drawings where:

FIG. 8A is a schematic representation of a Magic Angle Spinning system where a fluid saturated sample is placed in a rotor spinning about its axis and with its axis inclined at an angle 54.74° with respect to an externally applied magnetic field $B_0$;

FIG. 8B is a generic $T_1$ MAS 2D pulse sequence used in analyzing the sample of FIG. 8A;

BEST MODE(S) FOR CARRYING OUT THE INVENTION

Figure 1A:
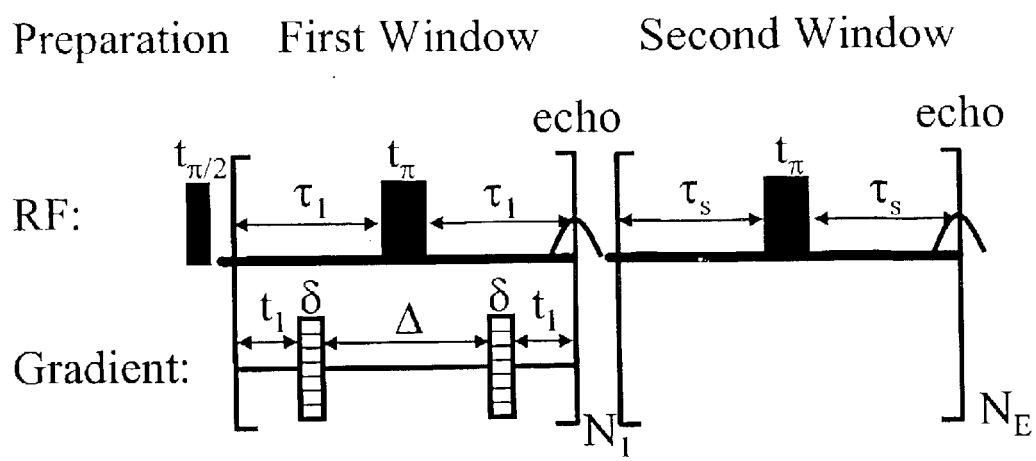
FIG. 1A is a schematic representation of a first generic series of Radio Frequency (RF) and Gradient pulse sequences utilized in the present invention to accommodate the uncoupling of diffusion effects from $T_2$ relaxation times in an NMR analysis.

Modified CPMG pulse sequences are applied to porous media containing fluids to determine various properties of the media and fluids. The modified CPMG pulse sequences allow various properties to be determined which previously have been undeterminable by prior methods due to the diffusion effects on $T_2$ relaxation time. These diffusion effects are particularly significant where large internal field gradients exist in fluids located in pore spaces of porous media.

Signals emitted from fluids and the media are analyzed to determine $T_2$ relaxation time (i.e. reflecting pore size), internal field gradient g, and amplitude which is proportional to the proton population. These properties are then plotted as 2D NMR maps to enhance the visualization of properties of the porous media and fluids contained therein. Similarly, diffusion coefficient distribution D can be determined and plotted in a 2D NMR map, where one axis is the $T_2$ relaxation time, a second axis is the diffusion coefficient distribution D, and the third axis is amplitude which is proportional to the proton population. In this 2D NMR map, water and crude oil are readily discernible thus allowing for the easy determination of water and oil saturation, as well as the oil viscosity and oil wettability.

These 2D maps may also be used to advantageously to display $T_1$MAS 2D NMR results.

Previous Approaches

Previous approaches for determining the internal field gradient g of fluids using regular CPMG pulse sequences have met with little success. For example, suppose a series of CPMG data is collected, each with a different echo spacing of $2\tau$, and an attempt is made to invert the internal field gradient distribution g of the porous system from this set of data. A common approach is to normalize all CPMG data with the smallest $\tau$:

$$\frac{M(t_i, \tau)}{M(t_i, \tau_s)} = \frac{\sum_j f_j e^{-t_i/T_j} \int_j P_j(g) e^{-\gamma^2 g^2 \tau^2 D t_i/3} dg}{\sum_j f_j e^{-t_i/T_j} \int_j P_j(g) e^{-\gamma^2 g^2 \tau_s^2 D t_i/3} dg} \quad (15)$$

where $\tau_s$ is the smallest $\tau$. If there is only one dominant pore size, or $P_j(g)$ is the same for all pore sizes, then the integral in the numerator can be factored out. The summation over different pore sizes can be cancelled, leaving. Eq.(15) with a set of decaying data on the LHS and the integral of internal field gradients on the RHS:

$$b_i = \frac{M(t_i, \tau)}{M(t_i, \tau_s)} = \int_j P_j(g) e^{-\gamma^2 g^2 \tau^2 D t_i/3} dg \quad (16)$$

Then the internal field gradient distribution g for the dominant pore size can be obtained through linear inversion using regularized routines. An example of such regularized routine is singular value decomposition (SVD) method. Algorithms for performing such analyses can be found in Numerical Recipes, Press, W. H., Flannery, B. P., Teukolsky, S. A., and Vettering, W. T., Cambridge University Press, (1988)).

While this approach works when there is only one dominant pore size, it is incapable of deducing internal field gradient distributions for all pore sizes. A problem exists as it is difficult to decouple the integral of internal field gradients g from the summation over the pore sizes. If a data inversion is carried out where there are multiple pore sizes, the inverted internal field gradient distribution would be a strange composite of contributions from all pore sizes with very ambiguous physical meaning.

Suppose the problem is addressed in a two-dimensional fashion in the following manner: Invert the CPMG echo trains and obtain all $T_2$ distributions with different echo spacings. Then these $T_2$ distributions may be displayed as a function of echo spacing along a dimension perpendicular to the $T_2$ relaxation time axis. Presumably, one would expect the $T_{2j}$ amplitude decays along the dimension of increasing echo spacing similar to the following:

$$f_j \int_j P_j(g) e^{-\gamma^2 g^2 \tau^2 D/3} dg \qquad (17)$$

where the factor $t_i$ in the exponent is temporarily ignored. Then, for each $T_{2j}$ (or each pore size), an internal field gradient distribution g is inverted from this set of data with varying echo spacing. The result would then be a 2D-plot of internal field gradient distribution g as a function of $T_{2j}$, or pore size. Unfortunately, this scheme does not work. With the regular CPMG data of different $\tau$'s, the inversion routines would not give a $T_2$ distribution with $$f_j \int_j P_j(g) e^{-\gamma^2 g^2 \tau^2 D/3} dg \qquad (17)$$

as an attenuated amplitude at $T_{2j}$ for increasing $\tau$, but rather, would push the amplitude to a shorter relaxation time, rendering it impossible to invert the internal field gradient distribution as a function of pore size. This is because the $t_i$ in the exponent inside the integral $$\int_j P_j(g) e^{-\gamma^2 g^2 \tau^2 D t_i/3} dg$$

is not separable from the echo train, and the inverted $t_{2j}$ amplitude would not be given by Eq. (17). Accordingly, a different approach is needed to solve the problem.

THEORETICAL BACKGROUND

A variety of NMR pulse sequences may be used in accordance with this invention to decouple the diffusion effects from the $T_2$ relaxation time in an NMR analysis. Modified CPMG pulse sequences have been discovered which allow the portion of the $T_2$ relaxation time, due to diffusion effect, to be quantified.

FIG. 1A schematically shows a first generic pulse sequence which allows $T_2D$ relaxation time to be uncoupled from the remainder of the overall $T_2$ relaxation time for fluids contained within a porous media. The pulse sequence shown in FIG. 1A may be referred to as a Relaxation-Diffusion 2D (RD2D) pulse sequence. The RD2D sequence consists of a preparation portion followed by a first window and a second window. The preparation portion is a 90° or $\pi/2$ pulse. The first window comprises a 180° or $\pi$ pulse and an echo spaced apart by a time $\tau_1$ which can be varied. The bracketed quantity in the first window is repeated $N_1$ times. Ideally, these echo spacing $2\tau_s$ are the smallest echo spacings allowed by the NMR instrument used to acquire the echo signals. This minimal echo spacing capability is generally specified by the manufacturer of the NMR instrument. The second window comprises a $\pi$ pulse and an echo spaced apart by a fixed time $\tau_s$, and the whole bracket is repeated $N_E$ times. Gradient pulses of time width $\delta$ can be applied on each side of the $\pi$ pulse in the first window.

Mathematically, this series of pulse sequences may be described by the following equations:

| | preparation | 1st window | 2nd window |
|---|---|---|---|
| RF: | $\left(\frac{\pi}{2}\right)_{\pm x}$ | $[-\tau_1 - \pi_y - \tau_1 - acq -]_{N_1}$ | $[-\tau_s - \pi_y - \tau_s - acg -]_{NE}$ |
| Gradient: | | $[-t_1 - G_k - \Delta - G_k - t_1 - -]_{N_1}$ | | where
 $\pi/2$ is a 90° pulse;
 $\pi$ is a 180° pulse;
 $G_k$ is a field gradient pulse of amplitude G having a time width of $\delta$;
 $\Delta$ is the time between two adjacent gradient pulses $G_k$ that are symmetrical about the $\pi$ pulses in the first window;
 Acq denotes acquisition of an echo signal;
 $N_1$ is the number of $\pi$ pulses applied in the first window;
 $N_E$ is the number of $\pi$ pulses applied in the second window;
 $t_1$ is the time delay between the $\pi/2$ pulse and the first gradient pulse;
 $\tau_1$ is one half of the echo spacing in the first window;
 $\tau_s$ is one half of the echo spacing in the second window;
 subscript x indicates a pulse is applied along the x-axis; and
 subscript y indicates a pulse is applied along the y-axis.

Figure 1B:
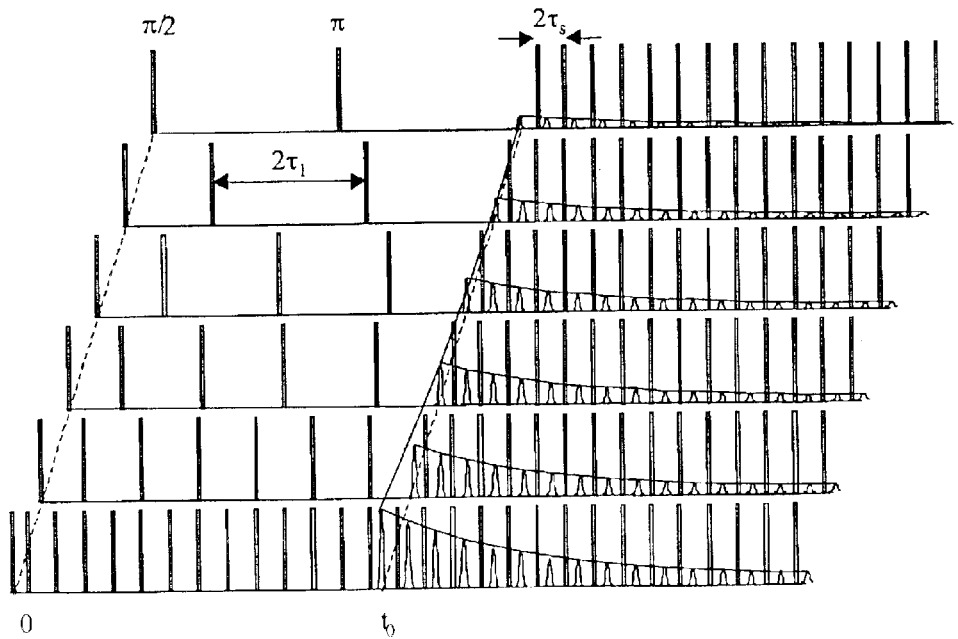
FIG. 1B is a schematic representation of a particular species of a generic series of pulses of FIG. 1A where the amplitudes of the gradient pulses are zero.

FIG. 1B illustrates a specific case of FIG. 1A where the amplitude of the gradient pulse is zero, i.e., no gradient pulse is applied in the overall series of pulses. As shown in FIG. 1B, an NMR pulse sequence is split into a preparation portion, a first window and a second window. The first window has a window width of $t_0$ where the echo spacing $2\tau_1$ is ideally varied from the smallest to the largest $\tau$ allowed, and the diffusion effect is encoded in the amplitudes corresponding to different relaxation times. Such information is collected in the second part of the pulse sequence using a regular CPMG pulse sequence and the smallest available $\tau_s$. This particular sequences of pulses is useful in determining the internal field gradient g for fluids in pore spaces of a porous media.

For purposes of clarity, each row of pulse sequences is shown sequentially offset in FIG. 1B. Ideally, the smallest possible echo spacing $2\tau_s$ is used the second part of the sequence such that diffusion effects are minimized. In the first part of the sequence, $2\tau_1$ is varied from the smallest to the largest values allowed.

If the time window for the first window is $t_0$, the i-th echo acquired by an NMR instrument in the second window of the sequence can be written as $$b_{li} = \sum_{j=1}^{N_R} f_{li} e^{-(t_0+t_i)/T_{2j}} + \varepsilon_i \quad \begin{array}{l} i = 1, \ldots, N_E \\ l = 1, \ldots, N_T \end{array} \qquad (18)$$

where $N_R$ is the number of $T_2$ relaxation times equally spaced on a logarithmic scale preselected for an inversion, $N_E$ is the number of echoes acquired in the second part of the sequence, $N_\tau$ is the number of different $\tau$'s, $b_{li}$ is the i-th echo of the l-th $\tau$ measurement, $\varepsilon_i$ is the noise for the i-th echo, and $f_{lj}$ the signal intensity associated with the relaxation time $T_{2j}$ of the l-th $\tau$ measurement. The term $f_{lj}$ can be further decomposed to $$f_{lj} = f_j^0 \sum_{k=1}^{N_g} P_{jk} e^{-\gamma^2 g_k^2 T_1^2 D t_0/3} + \varepsilon_l \quad \begin{array}{l} j = 1, \ldots, N_R \\ l = 1, \ldots, N_T \end{array} \qquad (19)$$

where $N_g$ is the number of gradient components, $g_k$ is a set of preselected gradient components equally spaced on a logarithmic scale, $N_R$ is the number of relaxation times equally spaced on a logarithmic scale, $f_j^0$ is the unattenuated pore volume fraction having a relaxation time $T_{2j}$ (i.e., $f_{lj}$ when $\tau \to 0$, or the smallest $\tau_s$), and $P_{jk}$ is the normalized volume fraction which has a gradient value of $g_k$ in the pore having a relaxation time $T_{2j}$. The $P_{jk}$ matrix gives the 2-D correlation distribution between the pore sizes and the internal gradients. It is the discretized form of $P_j(g)$ in Eq.(8).

Now that all echo trains are obtained with the same smallest $\tau_s$, the echo trains may be inverted. The $T_2$ distributions obtained are not shifted to shorter relaxation times, but instead, all information of the attenuation of the signal due to diffusion with different $\tau$'s within the first window of time length $t_0$ is contained in $f_{lj}$, which is proportional to the following:

$$f_j^0 \int_j P_j(g) e^{-\gamma^2 g^2 \tau^2 D t_i/3} dg \qquad (20)$$

Here $t_0$ is a constant, and is decoupled from the echo train measured in the second part of the sequence. In fact, $t_0$ need not be the same for different $\tau^l$ experiments, as long as a proper sampling is obtained of the variation of the exponential factor in Eq.(20).

Inversion Process

The inversion to obtain $P_{jk}$ can be accomplished by a two-step process, solving Eq.(18) and then Eq.(19), by using a singular value decomposition method, (Dunn, K. J, and LaTorraca, G. A, J. Magn. Reson., 140, 153 (1999)) and selecting the proper cutoff of singular values commensurate with the noise level. The acquired NMR measurement signal is frequently represented mathematically as a sum of exponentially decaying signals, each with an associated $T_2$ relaxation time. A set of $T_2$ relaxation times equally spaced in a logarithmic scale may be chosen prior to the actual measurement to cover the range of expected signals in a particular application. Thus, only the amplitudes associated with the exponentially decaying components with the pre-chosen $T_2$ relaxation times are to be solved. The system of equations is readily presentable as a matrix equation Ay=b which can be solved using standard software routines. The matrix A is formed by the exponential decay components at different pre-selected relaxation times $T_j$ and different decaying time $t_i$. The data vector b is formed by the echo train with each echo at different decaying time $t_i$. The vector y to be solved with elements of the amplitudes associated with different relaxation times. The singular value decomposition (SVD) method is one of such well-known methods for such solving of these equations. For example, the method is more fully described by Prammer, M. G., in U.S. Pat. No. 5,517,115, the teachings of which are hereby incorporated by reference in its entirety.

The inversion of matrix equation Ay=b using SVD, involves decomposing the matrix A into a product of three matrices, i.e., $A = UWV^T$, where U and V are orthonormal matrices, $V^T$ is the transpose of V, and W is a diagonal matrix containing diagonal elements called singular values and zero off-diagonal elements. These singular values are usually ordered in a monotonically decreasing manner, i.e., $W = \mathrm{diag}(\lambda_1, \lambda_2, \ldots, \lambda_m)$, where $\lambda_1 > \lambda_2 > \ldots > \lambda_m > 0$. To invert the matrix and obtain a solution y commensurate with a noise level $\sigma$, we usually ignore singular values less than $\lambda_r$, where $\lambda_r$ is determined by $(\lambda_1/\lambda_r) = |b|/\sigma$, $\lambda_1$ and $|b|$ being the largest singular value and the magnitude of the data vector, respectively.

However, if the $\tau_1$ values are not properly sampled, the error of the first inversion can seriously affect the accuracy of the second inversion.

Alternatively, to minimize the error due to two-step inversion process, a one-step global inversion process can be implemented by merging Eqs.(18) and (19) and solving $f_j^0 P_{jk}$ directly:

$$b_{li} = \sum_{j=1}^{N_R} \sum_{k=1}^{N_g} f_j^0 P_{jk} e^{-(t_0+t_i)/T_{2j}} e^{-\gamma^2 g_k^2 T_l^2 D t_0/3}, \quad \begin{array}{l} i=1,\ldots,N_E \\ l=1,\ldots,N_T \end{array} \qquad (21)$$

where the LHS is a vector $b_{li}$ with $N\tau \times N_E$ elements, and the RHS is a matrix of $(N_\tau \times N_E) \times (N_R \times N_g)$ multiplied by a vector $f_j^0 P_{jk}$ with $N_R \times N_g$ elements. The matrix size can be considerably reduced by compressing the spin echo data into a few windows (Dunn, K. J, and LaTorraca, G. A, J. Magn. Reson., 140,153 (1999)).

However, such a process creates a relatively large matrix and takes long iterative computations to obtain the result. Tests have shown that both one- and two-step inversions give similar results if the $\tau$ values are properly sampled within the window of $t_0$ and the inversion error is minimized.

The computation efficiency can be significantly improved by solving $f_j^0$ first using Eq.(18) and the data with the smallest $\tau$, and removing those columns where $f_j^0$'s are zero. This process alleviates difficulty because the value of $e^{-t_0/T_{2j}}$ can be so small that it reaches the limit of precision of the computer, causing problems in the inversion.

Method of Determining Properties

The following method employs principles of the above mathematical analysis to analyze properties of a porous medium containing fluids. First, a static magnetic field $B_0$ is applied by a NMR instrument to a porous medium containing fluids in pore spaces to polarize spins of protons in the porous medium and fluids and to create an overall magnetization. Subsequently, the NMR instrument applies a series of differentiated sequences of n radio-frequency (RF) pulses to the porous medium and fluids contained therein. The RF pulses are applied at the resonance frequency of the protons and at a given external magnetic field to excite the magnetization. These pulse sequences have a preparation part followed by a first window of a time length $t_0$ and a second window. The portion of the pulse sequence in the first window of at least one pulse sequence is differentiated by at least one differentiating variable $v_d$ from the portion of the pulse sequence in the first window of another of the pulse sequences.

Preferably, each of the pulse sequences in the first windows are varied from each other pulse sequence in the first window by varying the variable $v_d$. For example, in FIG. 1B, $v_d$ is $\tau_1$, which is of increasing time length in each of the l rows of pulses sequences.

The NMR instrument then acquires induced resonance signals from the porous medium and fluids contained therein during the second windows of the pulse sequences. The resonance signals are acquired as a function of $t_i$, $PA_1(t_i)$, and $v_d$, where $t_i$ is the time of the i-th spin echo in the second window as measured from initiation of that second window, $PA_1(t_i)$ is the spin echo amplitude, and $v_d$ is the value of the differentiating variable. In the example of FIG. 1B, the differentiating variable $v_d$ is $\tau_1$, which varies increasingly in time length in each of the l series or rows of pulse sequences.

The acquired induced resonance signals are processed as a function $t_i$, $PA_1(t_i)$, and $v_d$ to determine properties of the porous medium and fluids contained therein as a function of $T_2$, g, and $PA_3$ where $T_2$ is the transverse relaxation time of the protons, g is the internal field gradient in the pore spaces, and $PA_3$ is the amplitude proportional to proton population.

The processing step may include a first inversion and a second inversion. The first inversion inverts the signal as a function of $t_i$, $PA_1(t_i)$, and $v_d$ into values $T_2$, $PA_2$ and $v_d$. Subsequently, the second inversion inverts the values $T_2$, $PA_2$, and $v_d$, into $T_2$, $PA_3$, one of g and D.

$PA_1(t_i)$ corresponds to $b_{ij}$ of equation (18) and vd is one of the variables in the exponent of equation (19), i.e., $g_k$, $\tau_l$, and $t_0$. In this case, $\tau_l$ is the particular variable which is varied in the first window of the pulse sequences to create the differentiated attenuation in the second windows. The variable $t_i$ in equation (18) is $t_i$. With respect to values resulting from the first inversion, $T_2$ is $T_{2j}$ of equation (18), $PA_2$ is $f_{ij}$ in equation (18), and with respect to the results of the second inversion, $PA_3$ is $f_j^0 P_{jk}$ in equation (19). The mathematical inversion described above occurs in two steps and is carried out by a computer algorithm.

Alternatively, the processing step may be a single global inversion wherein $t_i$, $PA_1(t_i)$, and $v_d$ are inverted directly into $T_2$, $PA_3$, one of g and D. This corresponds to solving eqn. (21) for $f_j^0 P_{jk}$.

The use of the differentiated pulse sequences in the first windows of the pulse sequences and the initiation of the second windows at a time $t_0$ accommodates the uncoupled quantitative determination of transverse relaxation time $T_2$ of protons, the internal field gradients g, and amplitude proportional to proton population $PA_3$.

Referring again to the generic pulse sequence of FIG. 1A, the portions of the pulse sequences in the first windows of the pulse sequences have at least one of a plurality of $\pi$ pulses and a plurality of gradient pulses $G_k$. The $\pi$ pulses are spaced apart by echo spacing $2\tau_1$, and the gradient pulses $G_k$ are spaced apart by time $\Delta$ between gradient pulses and have an amplitude of G and a pulse width of $\delta$. The variable $v_d$ which may be varied in the first window may be any one of $\tau_1$, G, $\delta$, and $\Delta$. Again, in the example shown in FIG. 1B, $v_d$ which is varied was chosen as $\tau_1$ in each of the l-throw or pulse sequences.

FIG. 1B is the specific case of FIG. 1A wherein the RF pulse portion is applied and there is no gradient pulse portion applied. This is the case where the amplitude of the gradient pulse $G_k$ is zero.

In FIG. 1B, the portions of the pulse sequences in the second windows are generally identically to one another. Further, the pulse sequences in the second windows include a series of $\pi$ pulses having an echo spacing of $2\tau_s$. Ideally, these echo spacing $2\tau_s$ are the smallest echo spacings allowed by the NMR instrument used to acquire the echo signals. This minimal echo spacing capability is generally specified by the manufacturer of the NMR instrument. By minimizing the echo spacing $2\tau_s$, the diffusion effect between $\pi$ pulses in the second window are similarly minimized to enhance resolution.

Multi-Dimensional Display of Properties

These determined properties of $T_2$, g and $PA_3$ may be advantageously plotted as a 2D NMR map or plot. The values $T_2$, of g, and $PA_3$ are plotted on orthogonal axes to produce a 2D NMR plot to provide visualization of these properties of the porous medium and fluids contained therein. Preferably, the values $T_2$ and g are plotted on logarithmic scales.

Figure 2:
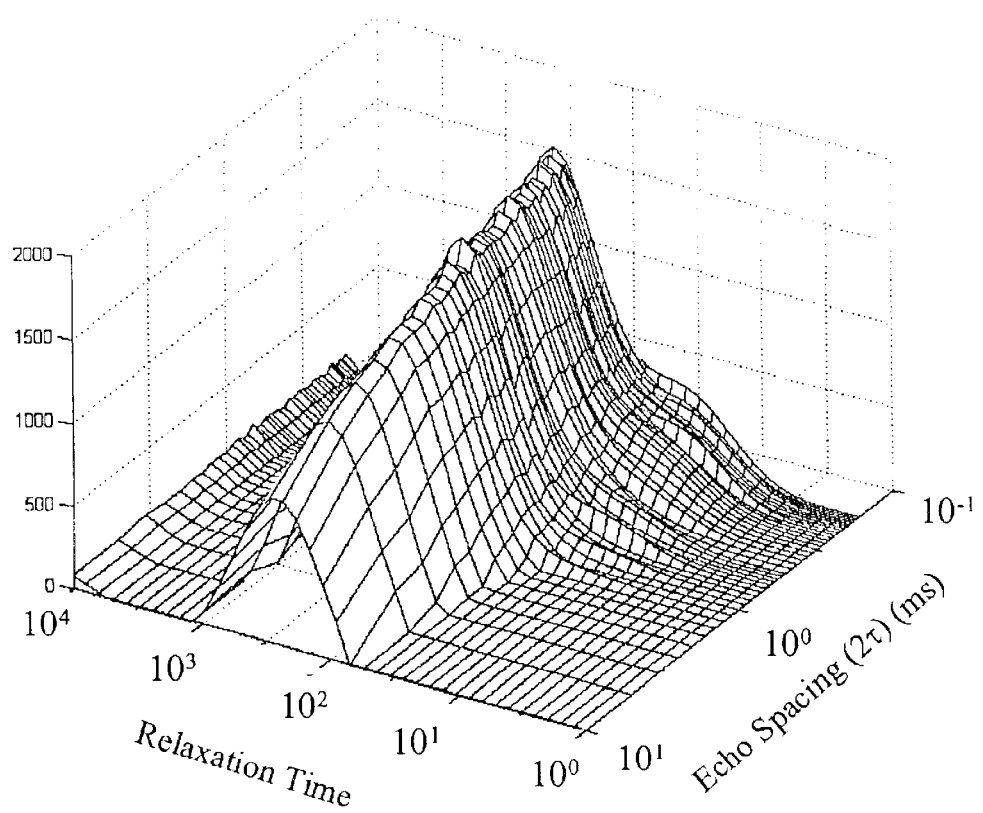
FIG. 2 is a 2D plot for a sandstone sample wherein an amplitude, which is proportional to proton population, is plotted as a function of $T_2$ distributions and echo spacing.

FIG. 2 shows the results of CPMG measurements for a water-saturated sandstone core sample using a MARAN ULTRA 2 MHz spectrometer. The detecting nuclei are hydrogen and its resonance frequency is about 2 MHz. A $t_0$ of 10.4 ms was chosen for the first windows of each of pulse sequences. The echo spacing $2\tau_1$ varies from 0.26 to 10.4 ms within the first part of window $t_0$, whereas in the smallest echo spacing $2\tau_s$, i.e., 0.26 ms was used for the second window. The initial $\pi/2$ and the $\pi$ pulses were 8.2 and 16.3 $\mu$s, respectively. The wait time between pulses sequences was 2 sec., and a total of 3072 echoes were acquired in the second part of the sequence. The signals were stacked 32 times with standard four phase cycling to improve the signal to noise ratio.

As shown in FIG. 2, a series of $T_2$ distributions which have been inverted from CPMG echo trains of different $\tau_i$'s are plotted along the TE (Time between Echoes) axis, going from the smallest to the largest echo spacing. At each relaxation time $T_{2j}$, the amplitude $f_{ij}$ is more or less monotonically decreasing as a function of increasing $\tau_i$, showing the enhanced relaxation due to diffusion effect from $e^{-\gamma^2 g^2 \tau_i^2 D t_0/3}$.

Figure 3:
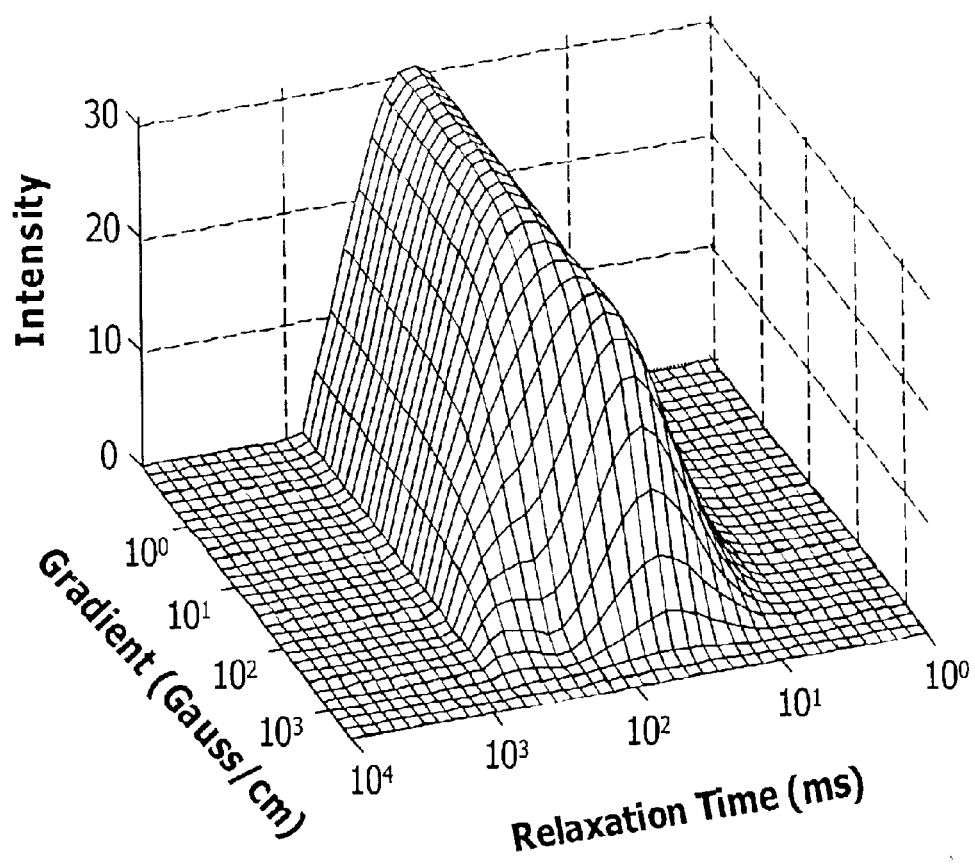
FIG. 3 is a 2D plot for the sandstone sample of FIG. 2 wherein the amplitude is plotted as a function of internal field gradient and $T_2$ relaxation time.

FIG. 3 shows an example of a brine-saturated sandstone core sample where moderate paramagnetic impurities are present. The experimental conditions are the same as those in FIG. 2. The 2-D plot displays the signal intensity (i.e., the vertical amplitude, or z axis, which is proportional to the proton population) as a function of $T_2$ relaxation times along one axis (representative of different pore sizes) and internal field gradients g along the other axis in the xy plane, both in logarithmic scale. The cross sectional view at a fixed $T_{2j}$ is the internal field gradient distribution g for that relaxation time (or pore size). The integration along the gradient axis at a fixed $T_{2j}$ gives the $T_2$ amplitude at that relaxation time. The total volume integral of the 2-D plot gives the porosity of the rock.

Figure 4:
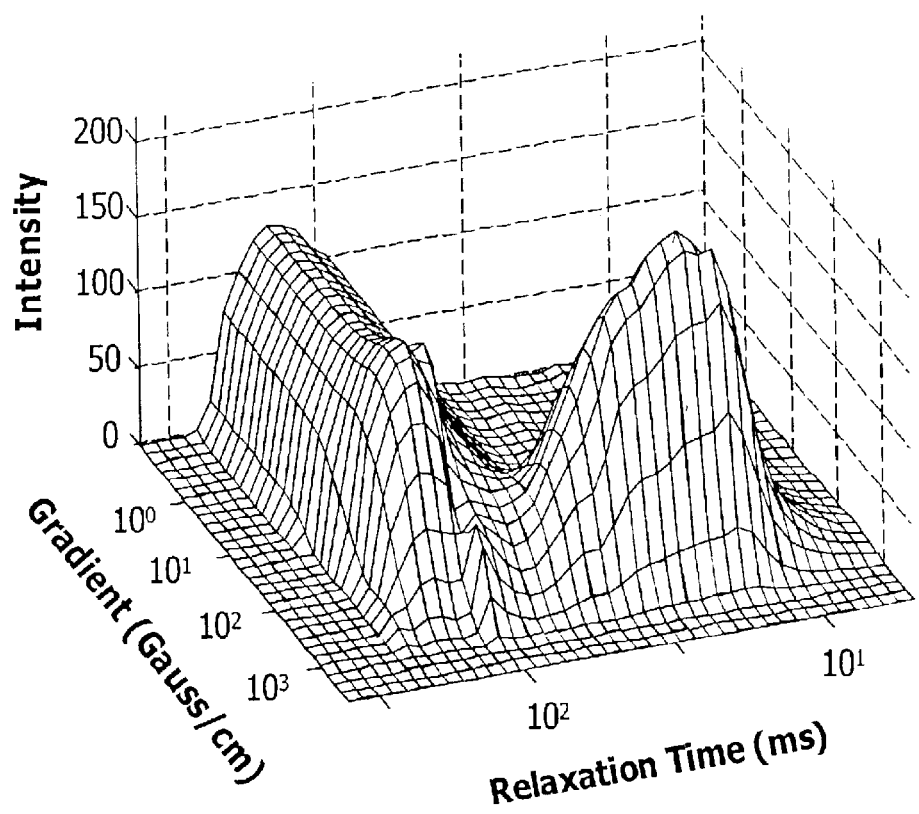
FIG. 4 is a 2D plot for a different sandstone sample wherein an amplitude, which is proportional to the proton population, is plotted as a function of internal field gradient and $T_2$ relaxation time.

FIG. 4 shows another example from a different sandstone sample. The experimental conditions were slightly different from those for FIGS. 2 and 3. The length of the first window $t_0$ was about 10.2 ms, and the echo spacing varies from 0.34 to 10.2 ms for the first window of the sequence. For the second window of the sequence, the echo spacing was 0.17 ms, the wait time was 1 sec., and a total of 6144 echoes were acquired. This sample has a bimodal $T_2$ distribution, with the small pores centered around 20 ms and the large pores centered around 150 ms. The small pores have a dominant peak of high internal gradients.

Figure 5:
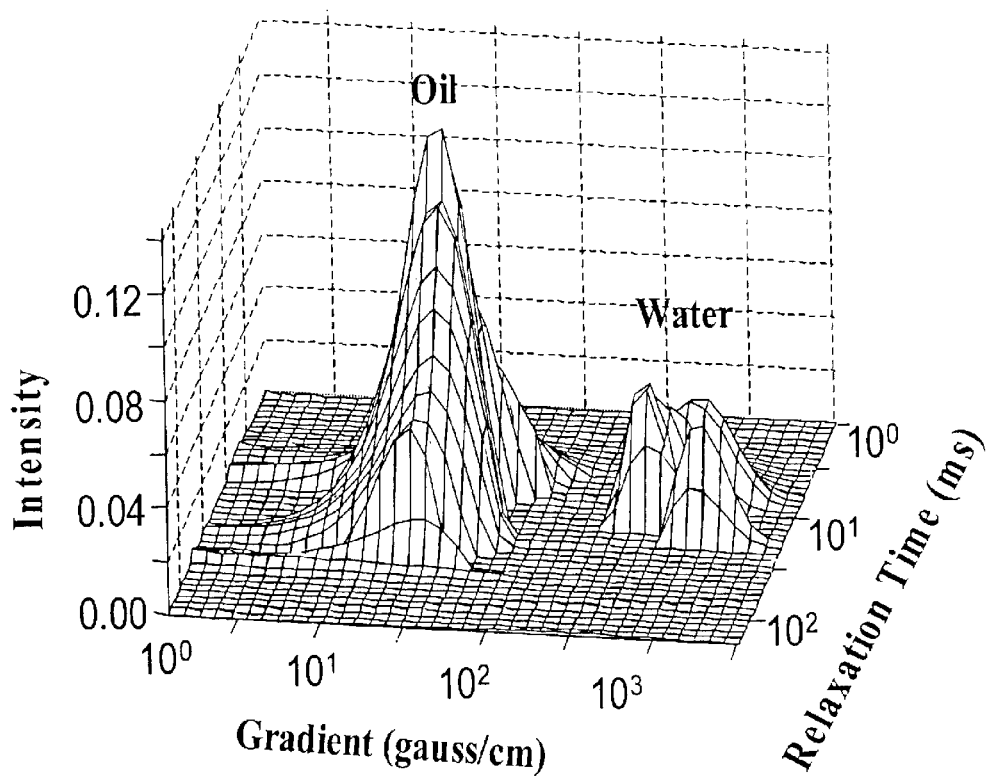
FIG. 5 is a 2D plot of an amplitude, which is proportional to proton population, is plotted as a function of internal field gradient and $T_2$ relaxation times for a diatomite sample saturated with both water and oil.

FIG. 5 is a 2D plot of the internal field gradient distributions g for different $T_2$ relaxation times (pore sizes) for a diatomite sample saturated with both water and oil, analyzed using a single diffusion coefficient for water. The peak located at the gradient value of about 20 gauss/cm corresponds to oil, whereas the peak located at the gradient value of about 800 gauss/cm corresponds to water.

Once the apparent internal magnetic field gradient distribution due to diffusion effect is known, one can substitute it back to Eqs. (18)–(20) and remove or reduce its adverse effect on the NMR signal through mathematical manipulations.

The 2D Scheme for Diffusion Coefficient Map

A similar analysis can be applied to obtain a 2-D plot with the $T_2$ relaxation time on one axis and the distribution of diffusion coefficients D of pore fluids on a second axis and amplitude which is proportioned to proton population on the third axis. This uncoupled determination can be accomplished by using pulsed field gradients applied between $\pi$ pulses during the first window.

Because the pulsed field gradients are significantly larger than the background gradients, a good estimate of the distributed diffusion coefficients can be obtained from the inversion of a suite of measurements of different τ's. Thus, instead of Eq.(19), now:

$$f_{lj} = f_j^0 \sum_{m=1}^{N_D} P_{jm}(D_m) e^{-\gamma^2 g^2 \delta^2 (\Delta_l - \delta/3) D_m t_0/3} + \varepsilon_l, \quad \begin{array}{l} j=1,\ldots,N_R \\ l=1,\ldots,N_\Delta \end{array} \quad (22)$$

where the unknown $P_{jm}$ to be solved is a distribution of diffusion coefficients $D_m$ covering a range of values, and $\Delta_l$ is the time between the pulsed gradients in the l-th pulse sequence, g is the amplitude of the pulsed field gradient, and δ is the pulse width for the gradients. Eq. (22) is the case in which the first window, as shown in FIG. 1A, contains a π pulse, with the pulsed field gradient $G_x$ applied on each side of the π pulse, and the varying parameters $v_d$ being δ, Δ, and G. For the case where the first window contains more than one π pulse, the equation is more complicated.

Figure 7:
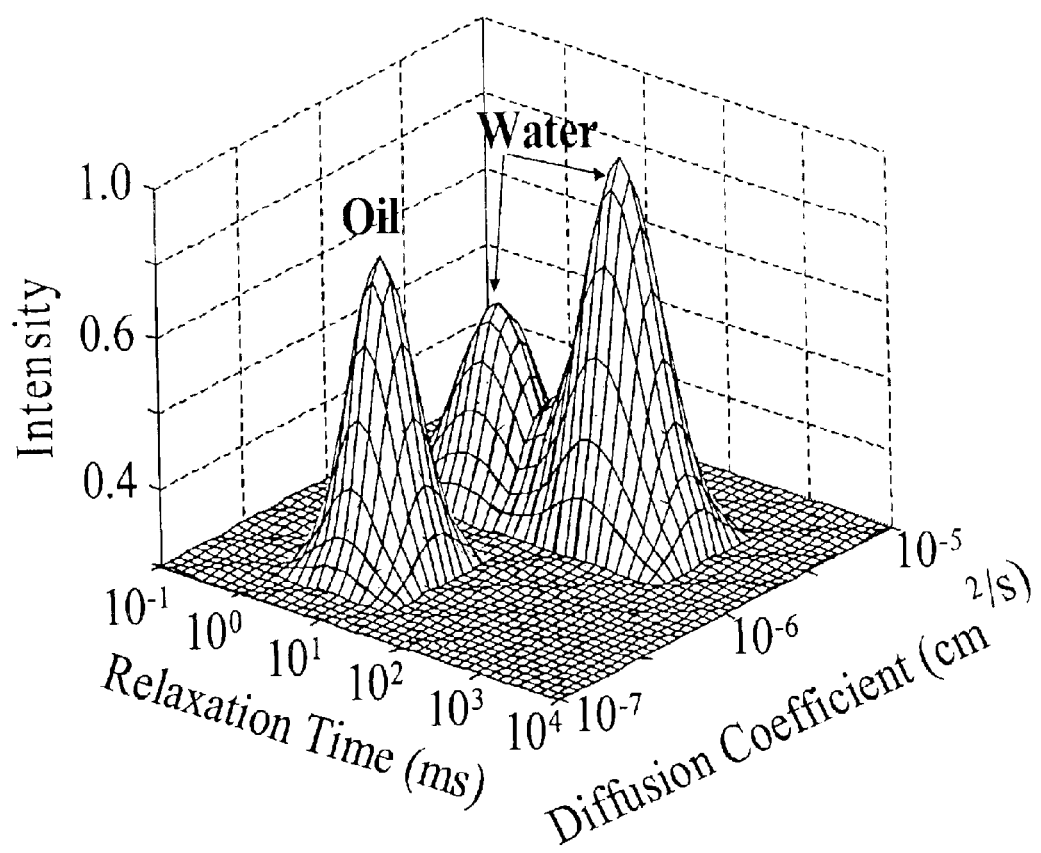
FIG. 7 is a schematic representation of an amplitude, which is proportional to proton population, plotted as a function of diffusion coefficient and $T_2$ relaxation time, wherein the water and oil signals are clearly separated in a 2D representation.

The result of this analysis is a 2-D plot with its vertical amplitude being proportional to the proton population as a function of $T_2$ relaxation times (i.e., pore sizes) on one axis, and the diffusion coefficients D (i.e., different pore fluids) on the other axis. FIG. 7 is a schematic illustration of a 2D NMR map showing amplitude proportional to proton population as a function of $T_2$ relaxation time and diffusion coefficient D for a core sample saturated by fluids.

Many properties of the porous medium and fluids contained therein can be obtained from the 2D NMR map. For example, the integration of the volume beneath the surface is proportional to the porosity of the core sample. As is apparent from FIG. 7, the diffusion coefficient D of oil is significantly different from that of water. Thus, it is possible to identify oil from water in this 2-D plot. The water saturation is given by the volume integral beneath the surface of the water signal. The oil saturation is given by volume integral beneath the oil signal. The viscosity of the oil can also be estimated by computing the logarithmic average of the $T_2$ distribution, $T_{2,LM}$, and correlating that to the viscosity η using the empirically determined relationship between $T_{2,LM}$ and η. If the oil peak shown at the 2D NMR map is at a relaxation time less than that in the empirical relationship determined in the laboratory for bulk oils, it can be inferred that the oil relaxation rate is enhanced by surface relaxation mechanism. Thus the oil wettability of the pore network of the porous medium, i.e., core sample, can be qualitatively estimated.

The techniques for obtaining the distribution of diffusion coefficients need not be limited to the use of pulsed field gradients described above. Other techniques, such as Tanner's stimulated echo technique (Tanner, J. E., J. Chem. Phys. 52, 2523 (1970)) with varying diffusion time, pulsed field gradient, or pulse width can be used in obtaining a distribution of diffusion coefficients (Lo, S-W, Hirasaki, G. J., House, W. V., and Kobayashi, R., SPE Paper 63217, Society of Petroleum Engineers, Dallas, Tex. (2000)).

Figure 6:
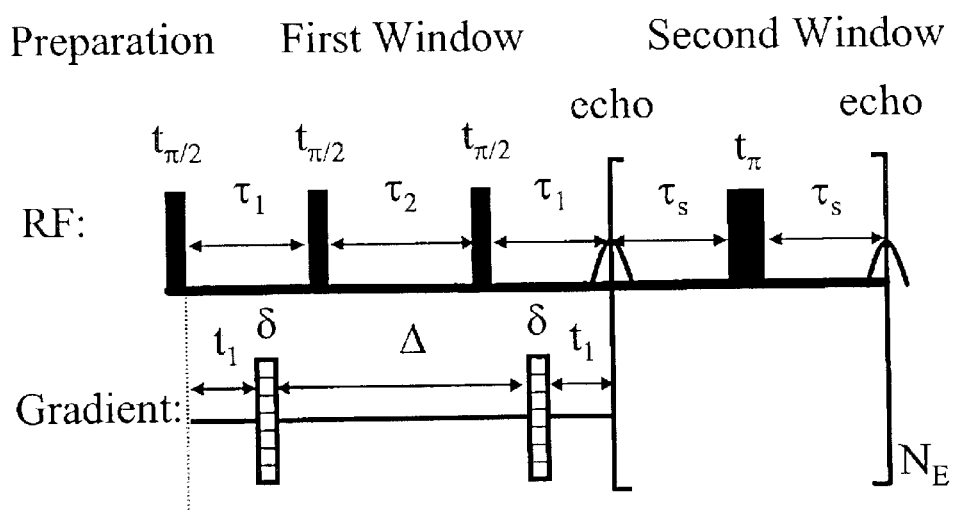
FIG. 6 is a schematic representation of a second generic series of Radio Frequency (RF) and Gradient pulse sequences which may be utilized in the present invention to determine diffusion coefficient distribution.

For example, Tanner's sequence is shown in FIG. 6. This sequence is a RD2D pulse sequence using stimulated echo. RD2D refers to a relaxation-diffusion 2D pulse sequence. Each pulse sequence comprises a preparation portion followed by first and seconds windows wherein the preparation portion is a π/2 pulse and the first window includes two π/2 pulses. The first π/2 pulse follows the initial π/2 pulse after a time $\tau_1$, the second π/2 pulse follows the first π/2 pulse by $\tau_2$, and an echo appears after a time $\tau_1$ from the second π/2 pulse; and a second window comprises a π pulse and an echo spaced apart by a fixed $\tau_s$, which is preferably the smallest echo spacing allowable by the NMR instrument, and the pulse sequence in the second window is repeated $N_E$ times. The gradient pulses of time width δ are applied during the $\tau_1$ periods in the first window.

Mathematically, this series of pulse sequences can be described by the following equations:

| preparation | 1st window | 2nd window |
|---|---|---|
| RF: $\left(\frac{\pi}{2}\right)_{\pm x}$ | $-\tau_1 - \left(\frac{\pi}{2}\right)_{\mp x} - \tau_2 - \left(\frac{\pi}{2}\right)_{\pm x}$ | $\begin{array}{l}-\tau_1 - acq - \\ \left[-\tau_s - \pi_y - \tau_s - acq - \right]_{NE}\end{array}$ |
| Gradient: | $-t_1 - G_k - - - - - \Delta - - - - - - G_k - t_1 - -$ | | where

π/2 is a 90° pulse;

π is a 180° pulse;

$G_k$ is a field gradient pulse of amplitude G having a time width of δ;

Δ is the time between two adjacent gradient pulses that are symmetrical about the two π/2 pulses in the first window;

Acq denotes acquisition;

$N_E$ is the number of π pulses applied in the second window;

$t_1$ is the time delay between the π/2 pulse and the first gradient pulse;

$\tau_1$ is the time between the initial π/2 pulse and the first π/2 pulse in the first window;

$\tau_2$ is the time between the first π/2 pulse and the second π/2 pulse in the first window;

$\tau_s$ is one half of the echo spacing (TE) in the second window;

subscript x indicates a pulse is applied along the x-axis; and subscript y indicates a pulse is applied along the y-axis.

3D Scheme of Display

A 3-D scheme is even possible where Eq. (22) is replaced by the full consideration of internal field gradients g and diffusion coefficient distributions D simultaneously. If the distribution of internal field gradients are significant, they can be incorporated into the data analysis using a global inversion scheme.

This is done by including the internal field gradients, $g_k$, in Eq.(22), and generalizing it into the following form:

$$f_{lj} = f_j^0 \sum_{k=1}^{N_g} \sum_{m=1}^{N_D} P_{jmk}(D_m, g_k) F(g, g_k, D_m, \Delta_l, \delta) + \varepsilon_l, \quad \begin{array}{l}j=1,\ldots,N_R \\ l=1,\ldots N_\Delta \\ k=1,\ldots,N_g\end{array} \quad (23)$$

where $$\ln[F(g, g_k, D_m\Delta_l, \delta)] = -\gamma^2 D_m\{^2\!/_3\tau^3 g_k^2 + \delta^2(\Delta - ^1\!/_3\delta)g^2 - \delta[(t_1^2+t_2^2) + \delta(t_1+t_2) + ^2\!/_3\delta^2 - 2\tau^2]g \cdot g_k\} \quad (24)$$

In this case, the variable $v_d$ may be chosen as any one of τ, G, δ, and Δ. The processing step may include a first inversion and a second inversion. The first inversion inverts the signal as a function of $t_i$, $PA_1(t_i)$, and $v_d$ into values $T_2$, $PA_2$ and $v_d$. The second inversion inverts values T2, PA2, and $v_d$, into $T_2$, $PA_3$, one of g and D. Alternatively, the processing step may use a global inversion wherein $t_j$, $PA_1(t_j)$, and $v_d$ are inverted directly into $T_2$, $PA_3$, one of g and D. The resulting 3D plot may include $T_2$, D and $PA_3$ plotted on the vertical axis while internal gradient g is plotted as a function of color such that all of the information may be displayed on a single plot.

$T_1$ MAS 2D NMR

The multi-dimensional representation of physical quantities in petrophysical analysis can be beneficial in other examples for the understanding of the characteristic properties of pore fluids in porous media. The representation of a $T_1$ MAS 2D NMR is an example which will now be described. Those skilled in the art will appreciate that a $T_2$ MAS 2D NMR may also be determined and displayed as well as the $T_1$ MAS 2D NMR.

Applying a magic angle spinning (MAS) technique to a fluid-saturated porous sample to eliminate the broadening due to the internal field has been done previously (Wilson, D. M. and LaTorraca, G. A., Paper 9923, International Symposium of the Society Core Analysts, Golden, Colo. (1999)). However, to analyze and display the data in a 2-dimensional plot, where one axis is the chemical shift, and the other axis is $T_1/T_2$ relaxation time, is new.

A $T_1/T_2$ measurement is performed in a MAS framework to obtain $T_1/T_2$ distribution (or pore size distribution). For convenience, a standard inversion-recovery pulse sequence is used to measure $T_1$ relaxation time. FIG. 8A is a schematic of a Magic Angle Spinning system where a core sample is placed in a rotor spinning about its axis and with its axis inclined at 54.74° with respect to the externally applied magnetic field $B_0$. FIG. 8B shows a $T_1$ MAS 2D sequence, wherein the preparation pulse θ can be either a π/2 pulse (saturation recovery) or a π pulse (inversion recovery), followed by a variable $T_1$ recovery time $\tau_1$, and then a π/2 pulse to get a Free Induction Decay (FID) signal.

Mathematically, this can be described by the following equation:

$$\theta - \tau_1 - \left(\frac{\pi}{2}\right)_\varphi - acq -$$

where

π/2 is a 90° pulse;

θ is one of a π pulse or saturation pulse;

Acq denotes acquisition window;

$\tau_1 = T_1$ recovery time; and

φ is the standard phase cycling list.

Figure 9:
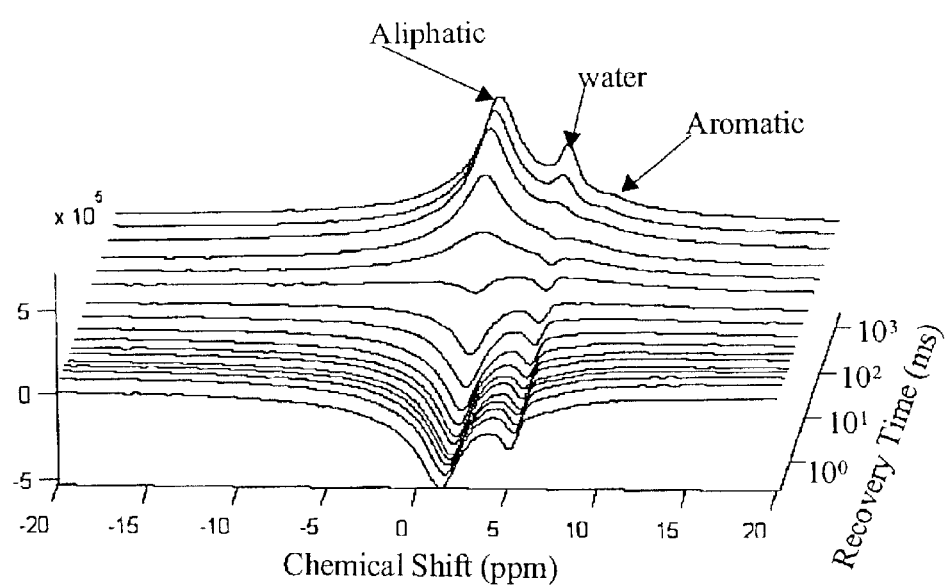
FIG. 9 illustrates a Fourier transformed chemical shift spectra of Free Induction Decay (FID) signals at different $T_1$ recovery times.

After the proton magnetization is inverted by the application of a π pulse, it starts to recover according to $(1-2e^{-tw/T_1})$, where $T_1$ is the longitudinal relaxation time constant and tw is the recovery time before the π/2 pulse. The π/2 pulse is used to produce the free-induction decay (FID) for signal reception. Because of magic angle spinning, the internal field undergoes periodic changes. When the internal field is positive, the magnetization starts to dephase, and it refocuses when the internal field becomes negative (similar to CPMG). At the end of each rotation cycle, spin echo appears in the FID, and is traditionally called rotational echo. In the MAS framework, the FID signal is a train of rotational echoes, and the Fourier transformation of the FID signal yields a high-resolution, water-oil-separated spectrum. The intensity of each peak is modulated by a factor of $(1-2e^{-tw/T_1})$. FIG. 9 is a Fourier transformed chemical shift spectra of the FID signals at different $T_1$ recovery times. The latter at different wait times are further inverted to obtain a 2D plot of $T_1$ relaxation time distribution versus chemical shift with the proton amplitude or intensity along the third dimension.

Figure 10:
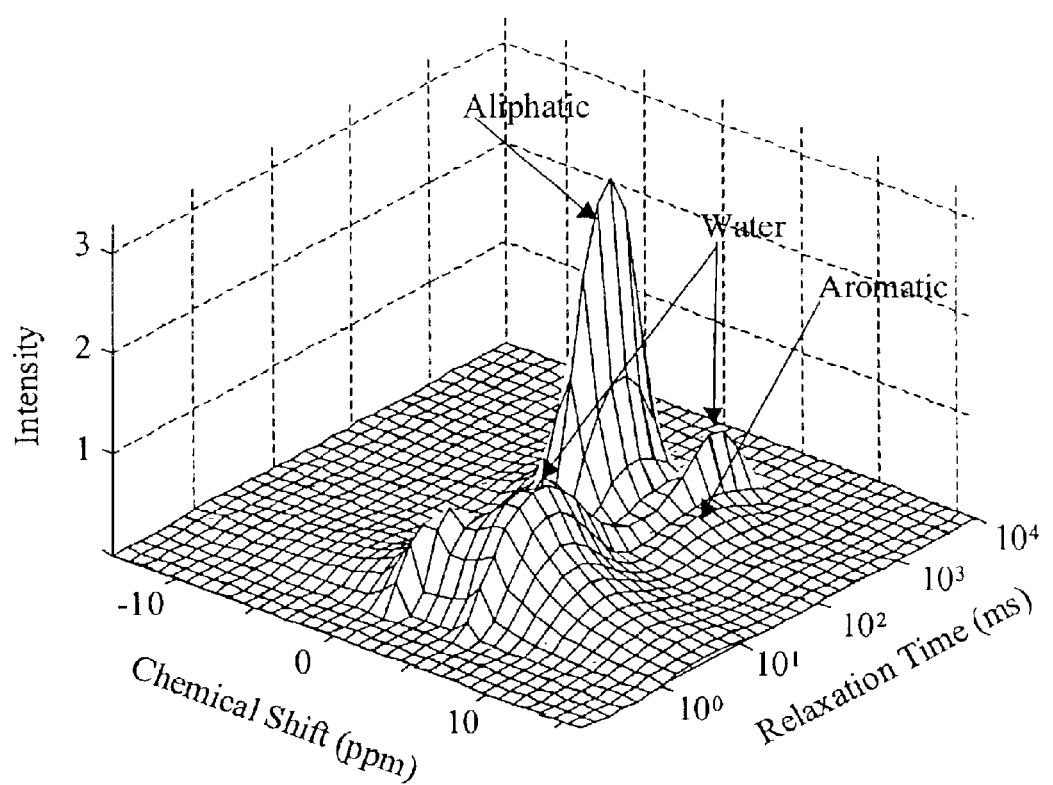
FIG. 10 is a 2D plot of an amplitude, which is proportional to proton population, as a function of $T_1$ relaxation time and proton chemical shift.

Using a set of recovery time twins, the $T_1$ recovery curve may be obtained for each peak in the high-resolution MAS spectrum, which can be expressed as $$s(\omega, tw_k) = \sum_n \sum_{j=1}^{N_R} a_{n,j} f_n(\omega - \omega_n) e^{-tw_k/T_{1,j}}, (k = 1, \dots, M) \quad (25)$$

where ω denotes frequency variable in a spectrum, $w_n$ is the frequency of n-th peak, $f(\omega-\omega_n)$ is the shape of the n-th peak, M is number of wait-times, $N_R$ is the number of pre-selected $T_1$ relaxation times, and $\alpha_{nj}$ the amplitude for n-th peak associated with the relaxation time $T_1$. If a $T_1$ inversion is performed for every frequency (chemical shift) in the spectrum, the sequential arrangement of all $T_1$ distributions along the chemical shift dimension yields a T1-MAS 2D spectrum of the rock sample. FIG. 10. is an example of T1 MAS 2D plot showing the aliphatic and aromatic peaks for oil and the peak for water.

While in the foregoing specification this invention has been described in relation to certain preferred embodiments thereof, and many details have been set forth for purpose of illustration, it will be apparent to those skilled in the art that the invention is susceptible to alteration and that certain other details described herein can vary considerably without departing from the basic principles of the invention.

What is claimed is:

1. A method for analyzing the properties of a porous medium containing fluids, the method comprising the steps of:

applying a static magnetic field $B_0$ to a porous medium containing fluids in pore spaces to polarize spine of protons in the porous medium and fluids and create an overall magnetization;

applying a series of differentiated pulse sequences including a combination of radio frequency (RF) and gradient pulses to the porous medium and fluids contained therein in the presence of the static magnetic field $B_0$ the pulse sequences having a preparation part followed by a first window and a second window, wherein the portion of the pulse sequence in the first window of at least one pulse sequence is differentiated by at least one differentiating variable $v_d$ from the portion of the pulse sequence in the first window of another of the pulse sequences;

acquiring induced resonance signals in the form of spin echoes from the porous medium and fluids contained therein during the second windows of the pulse sequences; and processing the acquired induced resonance signals to determine properties of the porous medium and fluids contained therein.

2. The method of claim 1 wherein:

the portions of the pulse sequences in the first windows of the pulse sequences have at least one of a plurality of π pulses and a plurality of gradient pulses $G_k$, the π pulses being spaced apart by echo spacing $2\tau_1$, and the gradient pulses $G_k$ having a spacing of Δ between gradient pulses and an amplitude of G and a pulse width of δ and the variable $v_d$ is one of $\tau_1$, G, δ, and Δ.

3. The method of claim 2 wherein:
the one of variable $v_d$ is $\tau_1$.
4. The method of claim 2 wherein:
the one of variable $v_d$ is G.
5. The method of claim 2 wherein:
the one of variable $v_d$ is $\delta$.
6. The method of claim 2 wherein:
the one of variable $v_d$ is $\Delta$.
7. The method of claim 1 wherein:
the resonance signals are acquired as a function of $t_i$, $PA_1(t_i)$, and $v_d$, where $t_1$ is the time of the $i_{th}$ spin echo in the second window, $PA_1(t_i)$ is $i_{th}$ spin echo amplitude, and $v_d$ is the value of the differentiating variable; and
the resonance signals are inverted into a function of $T_2$, one of g and D, and $PA_3$, where $T_2$ is the transverse relaxation time of the protons, g is the internal field gradient in the pore spaces, D is the diffusion coefficient of the fluids in the pore spaces, and $PA_3$ is an amplitude distribution proportional to proton population.
8. The method of claim 7 wherein:
the one of the properties of g and D which is determined is the internal field gradients g.
9. The method of claim 7 wherein:
the one of the properties of g and D which is determined is the diffusion coefficient D.
10. The method of claim 7 wherein:
the processing step includes a first inversion and a second inversion, the first inversion inverting the resonance signals as a function of $t_1$, $PA_1(t_1)$, and $v_d$ into values $T_2$, $PA_2$ and $v_d$, and the second inversion inverting values $T_2$, $PA_2$, and $v_d$, into $T_2$, $PA_3$, and one of g and D;
where $PA_2$ is an intermediary amplitude distribution as a function of $T_2$ and $v_d$.
11. The method of claim 7 wherein:
the processing step includes a global inversion wherein $t_1$, $PA_1(t_1)$, and $v_d$ are inverted directly into $T_2$, $PA_3$, and one of g and D.
12. The method of claim 1 wherein:
the portions of the pulse sequences in the second windows are generally identically to one another.
13. The method of claim 1 wherein:
the RF and gradient pulse sequences are described by the following equations:

preparation      1$^{st}$ window           2$^{nd}$ window

RF:    $\left(\frac{\pi}{2}\right)_{\pm x}$  $[-\tau_1 - \pi_y - \tau_1 - acq-]_{N_1}$   $[-\tau_s - \pi_y - \tau_s - acq-]_{NE}$ Gradient:       $[-t_1 - G_k - \Delta - G_k - -]_{N_1}$ where
$\pi/2$ is a 90° pulse;
$\pi$ is a 180° pulse;
$G_k$ is a field gradient pulse of amplitude G having a time width of $\delta$;
$\Delta$ is the time between two adjacent gradient pulses $G_k$ that are symmetrical about the $\pi$ pulses in the first window;
acq denotes acquistion;
$N_1$ is the number of $\pi$ pulses applied in the first windows;
$N_E$ is the number of $\pi$ pulses applied in the second window;
$t_1$ is the time delay between the $\pi/2$ pulse and the first gradient pulse;
$\tau_1$ is one half of the echo spacing in the first window;
$\tau_s$ is one half of the echo spacing in the second window;
subscript x indicates a pulse is applied along the x-axis; and
subscript y indicates a pulse is applied along the y-axis.
14. The method of claim 13 wherein:
the resonance signals are acquired as a function of $t_i$, $PA_1(t_i)$, and $v_d$, where $t_i$ is the time of the $I_{th}$ spin echo in the second window, $PA_1(t_i)$ is the $I^{th}$ spin echo amplitude, and $v_d$ is the value of the differentiating variable; and
the processing step includes a first inversion and a second inversion, the first inversion inverting the resonance signals as a function of $t_i$, $PA_1(t_i)$, and $v_d$ into values $T_2$, $PA_2$ and $v_d$, and the second inversion inverting values $T_2$, $PA_2$, and $v_d$, into $T_2$, $PA_3$, and one of g and D; where $T_2$ is the transverse relaxation time of the protons, g is the internal field gradient in the pore spaces, D is the diffusion coefficient of the fluids in the pore spaces, $PA_2$ is an amplitude distribution proportional to proton population and $PA_2$ is an intermediary amplitude distribution as a function of $T_2$ and $v_d$.
15. The method of claim 13 wherein:
the resonance signals are acquired as a function of $t_i$, $PA_1(t_i)$, and $v_d$, where $t_i$ is the time of the $I_{th}$ spin echo in the second window, $PA_1(t_i)$ is the $I^{th}$ spin echo amplitude, and $v_d$ is the value of the differentiating variable; and
the processing step includes a global inversion wherein $t_i$, $PA_1(t_i)$, end $v_d$ are inverted directly into $T_2$, $PA_3$, and one of g and D where $T_2$ is the transverse relaxation time of the protons, g is the internal field gradient in the pore spaces, D is the diffusion coefficient of the fluids in the pore spaces, and $PA_3$ is an amplitude distribution proportional to proton population.
16. The method of claim 1 wherein:
the RF and gradient pulse sequences are described by the following equations:

RF:    $\left(\frac{\pi}{2}\right)_{\pm x} - \tau_1 - \left(\frac{\pi}{2}\right)_{\mp x} - \tau_2 - \left(\frac{\pi}{2}\right)_{\pm x}$   $\begin{array}{c}-\tau_1 - acq-\\ [-\tau_s - \pi_y - \tau_s - acq-]_{NE}\end{array}$ Gradient:                $[-t_1 - G_k - \Delta - G_k - t_1]$ preparation     1$^{st}$ window           2$^{nd}$ window where
$\pi/2$ is a 90° pulse;
$\pi$ is 180° pulse;
$G_k$ is a field gradient pulse of amplitude G having a time width of $\delta$;
$\Delta$ is the time between two adjacent gradient pulses that are symmetrical about the two $\pi/2$ pulses in the first window;
acq denotes acquistion;
$N_E$ is the number of $\pi$ pulses applied in the second window;
$t_1$ is the time delay between the $\pi/2$ pulse and the first gradient pulse;
$\tau_1$ is the time between the initial $\pi/2$ pulse and the first $\pi/2$ pulse in the first window;
$\tau_2$ is the time between the first $\pi/2$ pulse and the second $\pi/2$ pulse in the first window;

$\tau_g$ is one half of the echo spacing (TE) in the second window;

subscript x indicates a pulse is applied along the x-axis; and subscript y indicates a pulse is applied along the y-axis.

17. The method of claim 16 wherein:

the resonance signals are acquired as a function of $t_I$, $PA_1(t_I)$, and $v_d$, where $t_1$ is the time of the $I_{th}$ spin echo in the second window, $PA_1(t_I)$ is the $I^{th}$ spin echo amplitude, and $v_d$ is the value of the differentiating variable; and the processing step includes a first inversion and a second inversion, the first inversion inverting the signal as a function of $t_I$, $PA_1(t_I)$, and $v_d$ into values $T_2$, $PA_2$ and $v_d$, and the second inversion inverting values $T_2$, $PA_2$, and $v_d$, into $T_2$, $PA_3$, and one of g and D;

where $T_2$ is the transverse relaxation time of the protons, g is the internal field gradient in the pore spaces, D is the diffusion coefficient of the fluids in the pore spaces, $PA_2$ is an intermediary amplitude distribution as a function of $T_2$ and $v_d$ and $PA_3$ is an amplitude distribution proportional to proton population.

18. The method of claim 16 wherein:

the resonance signals are acquired as a function of $t_i$, $PA_1(t_i)$, and $v_d$, where $t_i$ is the time of the $i_{th}$ spin echo in the second window, $PA_1(t_i)$ is the $i^{th}$ spin echo amplitude, and $v_d$ is the value of the differentiating variable; and the processing step includes a global inversion wherein $t_i$, $PA_1(t_i)$, and $v_d$ are inverted directly into $T_2$, $P_2$, and one of g and D where $T_2$ is the transverse relaxation time of the protons, g is the internal field gradient in the pore spaces, D is the diffusion coefficient of the fluids in the pore spaces, and $PA_3$ is an amplitude distribution proportional to proton population.

19. The method of claim 16 wherein:

the variable $v_d$ is one of $\tau_1$, $\tau_2$, G, $\delta$, and $\Delta$.

20. The method of claim 19 wherein:

the one of variable $v_d$ is $\tau_1$.

21. The method of claim 19 wherein:

the one of variable $v_d$ is $\tau_2$.

22. The method of claim 19 wherein:

the one of variable $v_d$ is G.

23. The method of claim 19 wherein:

the one of variable $v_d$ is $\delta$.

24. The method of claim 19 wherein:

the one of variable $v_d$ is $\Delta$.

25. A computer storage medium storing a software program to be executed on a computer to control an NMR instrument, comprising:

a first software application which implements the following:

application by an NMR instrument of a static magnetic field $B_0$ to a porous medium containing fluids in pore spaces to polarize spins of protons in the porous medium and fluids and create an overall magnetization;

application by the NMR instrument of a series of differentiated pulse sequences in the presence of the static magnetic field $B_0$, the pulse sequences including a combination of radio-frequency (RF) and gradient pulses to the porous medium and fluids contained therein, the pulse sequence having a preparation part followed by a first window and a second window, wherein the portion of the pulse sequence in the first window of at least one pulse sequence is differentiated by at least one differentiating variable $v_d$ from the portion of the pulse sequence in the first window of another of the pulse sequences;

acquiring, through the use of the NMR instrument, induced resonance signals from the porous medium and fluids contained therein; and processing the acquired induced resonance signals to determine properties of the porous medium and fluids contained therein.

26. The computer storage medium of claim 25 wherein:

the portions of the pulse sequences in the first windows of the pulse sequences have at least one of a plurality of $\pi$ pulse and a plurality of gradient pulses $G_k$, the $\pi$ pulses being spaced apart by echo spacing $2\tau_i$, and the gradient pulses $G_k$ having a spacing of $\Delta$ between gradient pulses and an amplitude of G and a pulse width of $\delta$ wherein the variable $v_d$ is one $\tau_i$, G, $\delta$, and $\Delta$.

27. The method or claim 25 wherein:

during the second windows of the pulse sequences, the resonance signals are acquired as a function of $t_i$, $PA_1(t_i)$, and $v_d$, where $t_i$ is the time of the $I_{th}$ spin echo in the second window as measured from initiation of that second window, $PA_1(t_i)$ is the spin echo amplitude at time $t_i$, and $v_d$ is the value of the differentiating variable; and the resonance signals are inverted into a function of $T_2$, one of g and D, and $PA_3$, where $T_2$ is the transverse relaxation time of the protons, g is the internal field gradient in the pore spaces, D is the diffusion coefficient of the fluids in the pore spaces, and $PA_3$ is an amplitude distribution proportional to proton population.

* * * * *